(12) United States Patent
Nemcik

(10) Patent No.: US 7,784,115 B1
(45) Date of Patent: Aug. 31, 2010

(54) FOOT ALIGNMENT SOCKS

(76) Inventor: Eva Nemcik, 8130 Springer Dr., Kirtland, OH (US) 44094-9538

( * ) Notice: Subject to any disclaimer, the term of this patent is extended or adjusted under 35 U.S.C. 154(b) by 219 days.

(21) Appl. No.: 11/900,041

(22) Filed: Sep. 10, 2007

(51) Int. Cl.
A41B 11/00 (2006.01)
A43B 17/00 (2006.01)
A41D 27/12 (2006.01)

(52) U.S. Cl. .................................. 2/239; 2/61
(58) Field of Classification Search ............ 2/61, 2/239, 240, 241, 242; 602/30; 36/95; 128/893
See application file for complete search history.

(56) References Cited

U.S. PATENT DOCUMENTS

| | | | | | |
|---|---|---|---|---|---|
| 715,543 | A | * | 12/1902 | Bosworth | 2/239 |
| 1,999,929 | A | * | 4/1935 | Hearn | 2/239 |
| 5,623,734 | A | * | 4/1997 | Pugliatti | 2/239 |
| 5,699,557 | A | * | 12/1997 | Johnson | 2/239 |
| 6,142,785 | A | * | 11/2000 | Williams | 434/205 |
| 6,318,373 | B1 | * | 11/2001 | Kasahara | 128/894 |
| 6,334,222 | B1 | * | 1/2002 | Sun | 2/239 |
| 7,107,626 | B1 | * | 9/2006 | Andrews | 2/239 |
| D548,951 | S | * | 8/2007 | Paulin | D2/980 |
| D581,654 | S | * | 12/2008 | Miliotis | D2/980 |

* cited by examiner

Primary Examiner—Gary L Welch
Assistant Examiner—Amber R Anderson
(74) Attorney, Agent, or Firm—Christine A. Flanagan; Roetzel & Andress

(57) ABSTRACT

Foot Alignment Socks are a uniquely designed adaptation of regular socks used to alleviate minor foot problems. Foot Alignment Socks differ from traditional socks in that there is no covered toe assembly. Instead the socks have four separators which fit in between the toes. They are cylindrical and sturdy yet soft and yielding as they are constructed from the same fabric as the body of the sock. The separators stretch and align toes into proper position in respect to the rest of the foot. This toe alignment counters the harmful effects of daily foot compression and stress caused by tight and ill-fitting shoes as well as relieving foot pain from excess walking, standing, jogging, or strenuous sports and activities. With consistent use Foot Alignment Socks soothe and straighten crooked and deformed toes. They are ideal as an over-night foot maintenance treatment.

13 Claims, 5 Drawing Sheets

SIDE VIEW

CROSSECTION A-A

FOOT ALIGNMENT SOCKS

RELATED APPLICATIONS

This application claims priority from U.S. Provisional Patent Application No. 60/843,952 filed on Sep. 12, 2006.

BACKGROUND OF THE INVENTION

Variety of devises for stretching, aligning and separating toes are known in prior art. U.S. Pat. Nos.: 7,131,939, 7,107, 626 B1. Prior art devices are mostly for Yoga or they are exercise tools, which follows the same idea to align, separate and stretch the toes. Several tools for toe alignment and separation are recently on the market. Heretofore devices are all designed to address one specific foot problem. They are either plastic braces, elastic loops with foam pad bottoms, individual foam toe cushions or individual toe caps. They are effective and truthful to their claims, but they are very user unfriendly, difficult to apply or keep them on.

None of the Prior Art devices provide comfortable soothing and relaxed feeling as the present invention while mounted on users' feet. The present invention not only that helps relive foot pain from different foot discomforts, but also conditions feet to prevent foot problems to occur due to daily foot overuse and daily foot stress. It will maintain and support proper foot health.

BRIEF SUMMARY OF THE INVENTION

The present invention is directed to socks, namely to Foot Alignment Socks, which are meant to be worn after being on feet all day long. These socks have 4 toe separators from the material of the sock which forms 5 openings for toes to be stretches out. These separators have a function to apply gentle pressure on misaligned toes and position them into proper alignment with rest of the foot into position where nature intended them to be. Proper foot alignment helps to eliminate numerous foot, knee and hip problems. Toe separators are soft on touch, but sturdy inside to provide user friendly and easy application which accommodates longer wearing period which can be as long as overnight. Longer term wearing increases effectiveness of the invention. Therefore, it can be appreciated that there exists a continuing need for a new and improved foot alignment device that is easier to mount, keep on and take off. In this regard, the present invention substantially fulfills the need for user-friendlier device.

DETAILED DESCRIPTION OF THE INVENTION

Figure 1:
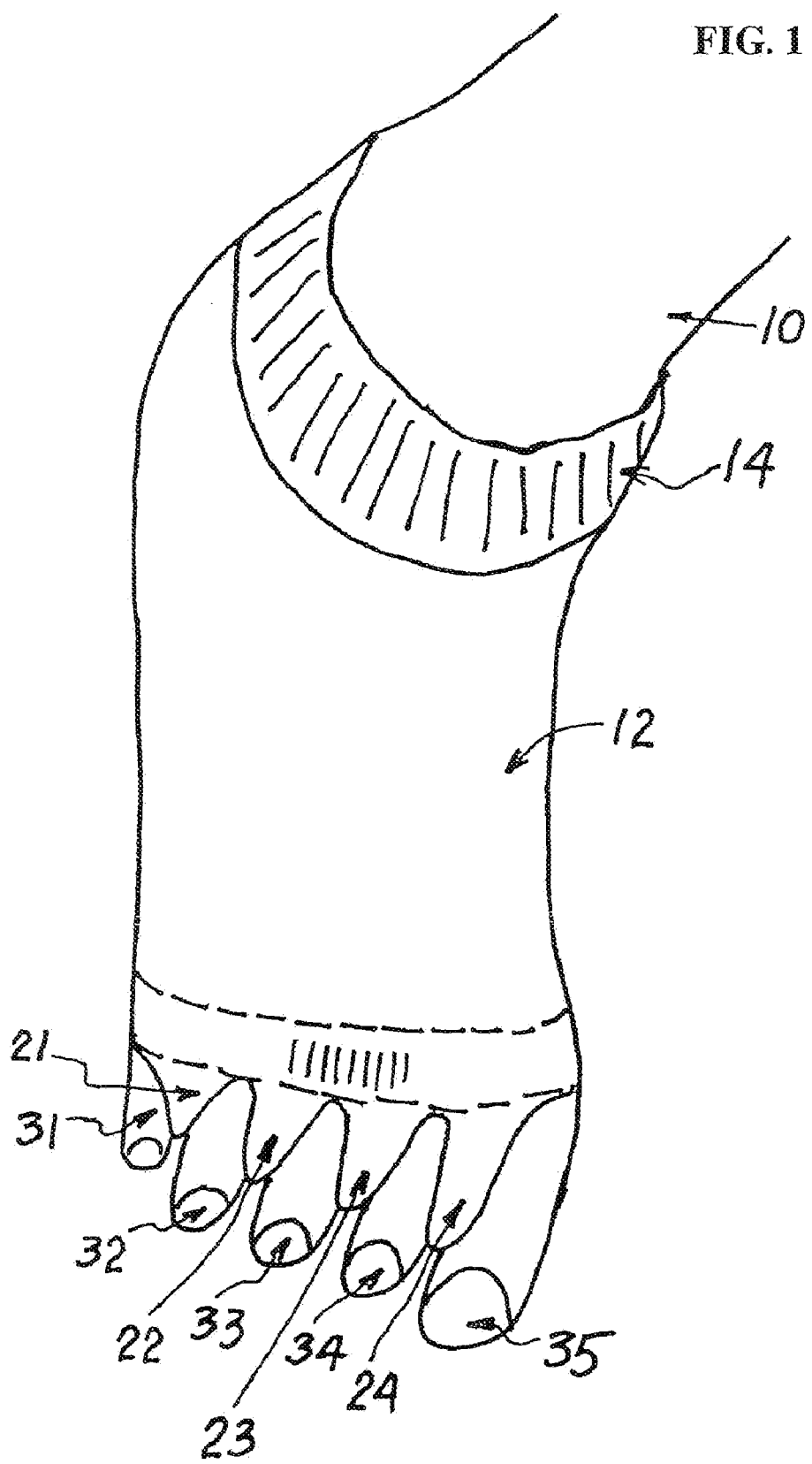
FIG. 1 is a top side view of a right foot of a user wearing sock constructed according to the teachings of the present invention.

Referring now to the drawings in greater detail there is shown in FIG. 1 a right foot of a user of a sock 12 which is constructed according to the teachings of the present invention and which is mounted on the foot 10. In this embodiment, the sock 12 has a short ankle bend 14 and is made material of choice such as cotton, acrylic cashmere, nylon, Lycra and spandex blend. It is to be noted that selection of materials has no effect on intention of this invention. FIG. 1 Is showing the users right foot 10, mounted on sock 12 where toes 31, 32, 33, 34, and 35 are separated by separators 21, 22, 23, and 24.

Figure 2A:
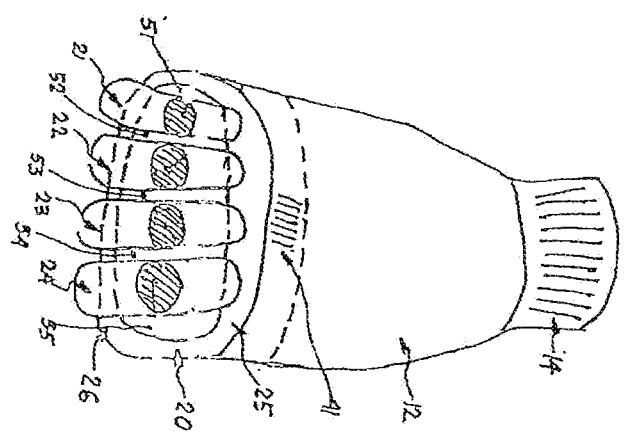
FIG. 2A is a front overhead view of the sock shown in FIG. 1 but without the foot of the user and showing four separators in place.
Figure 2B:
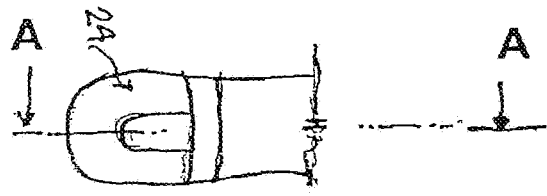
FIG. 2B. is a side view of the sock shown in FIG. 1 but without the foot of the user.
Figure 2C:
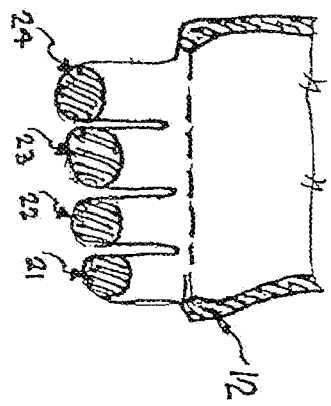
FIG. 2C. is a cross sectional view from direction of line A-A of FIG. 2B.

FIG. 2 illustrates the front end of the sock body 20 which has five openings 51, 52, 53, 54 and 55 created by separators 21, 22, 23 and 24 extended from the top 25 of the sock to the sole of the sock 26. The toes of the user, when socks are mounted, extend through openings 51, 52, 53, 54, and 55 to achieve claimed feature of the invention. The separators 21, 22, 23 and 24 of circular cross-section are of the same or similar material as the sock 12. The diameters and lengths of separators varies according the locations of separators on the sock. Separator 21 is extending 25 MM from the end 20 of the sock 12. The separator 21 diameter is 12.5 (+2/−2) MM. The separator 22 is extending 30 MM from the end 20 of the sock 12. The separator 22 diameter is 12.5 (+2/−2) MM. The separator 23 is extending 30 MM from the end 20 of the sock 12. The separator 23 diameter is 12.5 (+2/−2) MM. The separator 24 is extending 35 MM from the end 20 of the sock 12. The separator 24 diameter is 15 (+2/−2) MM.

Figure 3:
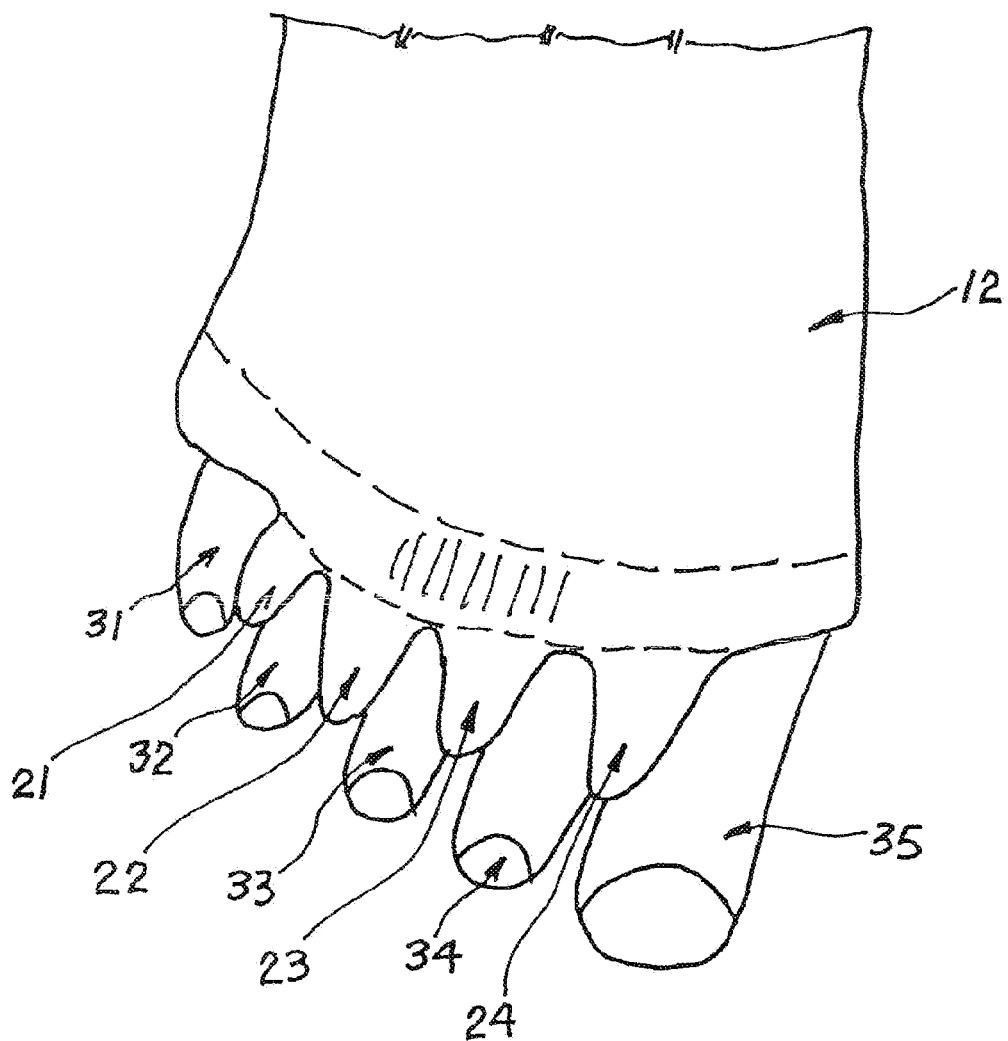
FIG. 3 is a detail top front view on the right sock mounted on user's foot.

FIG. 3 is showing detail positions of mounted toes 31, 32, 33, 34 and 35, versus separators 21, 22, 23 and 24. Separator 21 is separating small toe 31 from the fourth toe 32. Separator 22 is separating the fourth toe 32 from the third toe 33. Separator 23 is separating the third toe 33 from the second toe 34 and the separator 24 is separating the second toe 34 from the big toe 35.

FIG. 1, FIG. 2 and FIG. 3 show the right foot sock.

Figure 4:
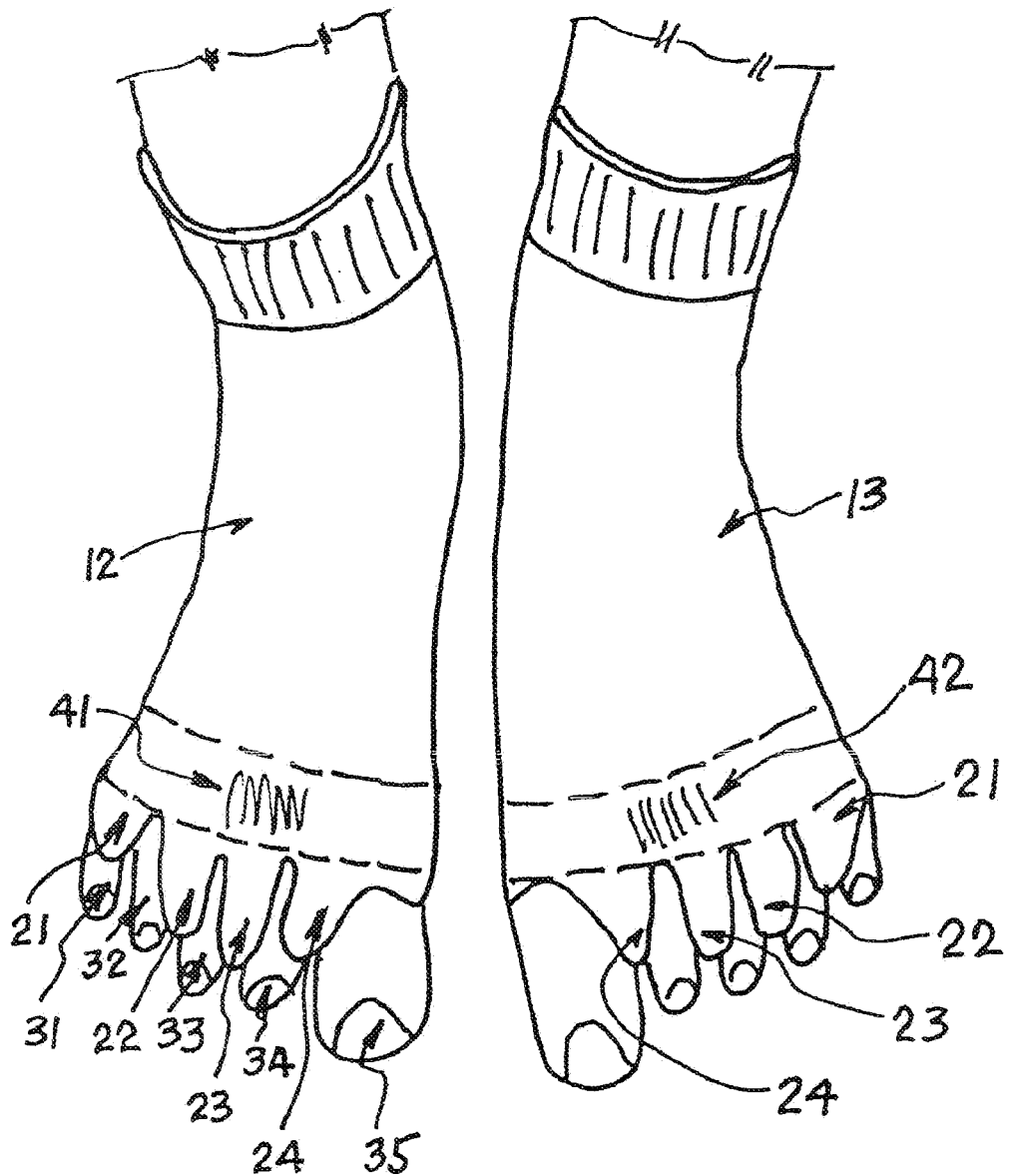
FIG. 4 is a top front view of the right and left alignment socks mounted on user's feet.
Figure 5:
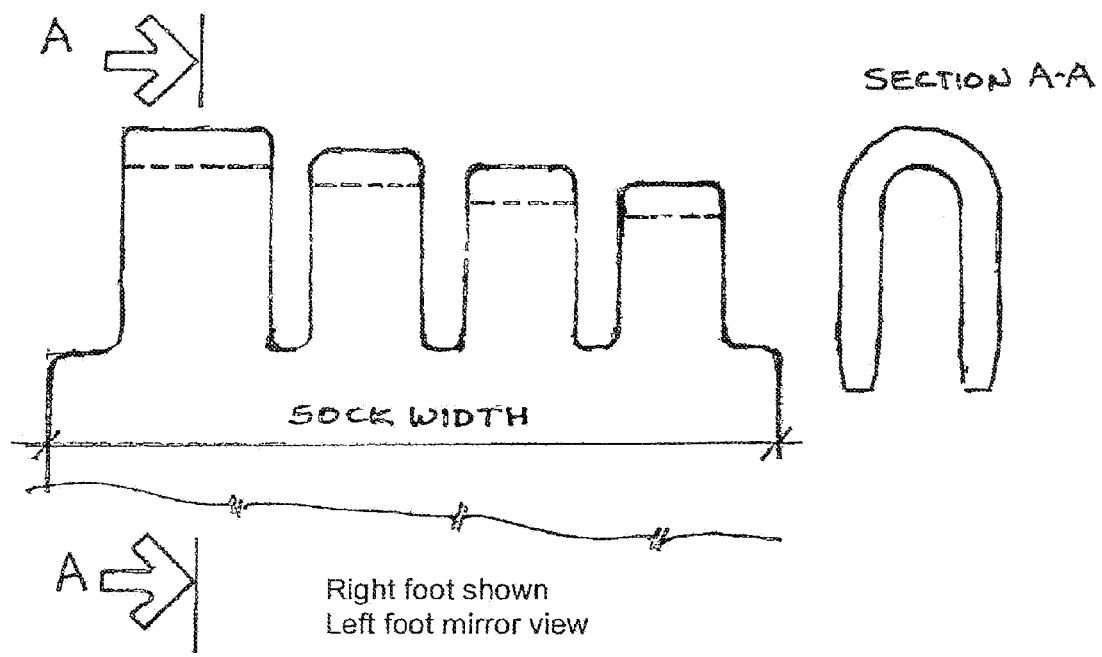
FIG. 5 is a detail top front view of the toe separators and a cross sectional view from the direction of line A-A.

FIG. 4 shows location of separators on the right sock 12 and left sock 13. The left foot sock 13 is a mirror image of the right foot sock 12 to accommodate left foot configuration. The right and left sock is recognizable by different embroidery 41 and 42 on the top of each sock. This way it is easy to recognize and mount on the right and the left foot.

The Foot Alignment Socks 12 and 13 of present invention has advantages over the current systems of plastic molded devices. These advantages are that the socks are easily mounted; stay on foot and after short period of training may be worn overnight which increases effectiveness of the device. The socks are washable and therefore useable for extended period. The result of the usage is foot stress relief and pain relief due to the minor foot misalignment. Accordingly, the scope of the present invention is only to be limited as necessitated by the accompanying claims.

What is claimed is:
1. A pair of foot alignment socks comprising:
   a left sock and a right sock, each sock comprising:
      a sock body generally configured to substantially cover a foot and having a first open end positionable proximate to the base of the toes of the foot, an upper portion which extends over the top of the foot, a lower portion which extends over the sole of the foot, a heel portion which extends over a heel of the foot, and a second open end positionable proximate to the ankle attached to the foot;
      a first toe separator attached to the first open end of the sock body and which extends from the upper portion of the sock body to the lower portion of the sock body at a position between a first toe and a second toe of a foot in the sock body;

a second toe separator attached to the first open end of the sock body and which extends from the upper portion of the sock body to the lower portion of the sock body at a position spaced from the first toe separator and between a second toe and a third toe of a foot in the sock body;

a third toe separator attached to the first open end of the sock body and which extends from the upper portion of the sock body to the lower portion of the sock body at a position spaced from the second toe separator and between a third toe and a fourth toe of a foot in the sock body;

a fourth toe separator attached to the first open end of the sock body and which extends from the upper portion of the sock body to the lower portion of the sock body at a position spaced from the third toe separator and between a fourth toe and a fifth toe of a foot in the sock body;

the first, second, third and fourth toe separators being generally cylindrical and extending outward from the first open end of the sock body and defining five distinct openings in the first open end of the sock body; and the first toe separator has a greater diameter than the second, third and fourth toe separators.

2. The pair of foot alignment socks of claim 1, wherein the sock material is chosen from the group of cotton, acrylic cashmere, nylon and spandex.

3. The pair of foot alignment socks of claim 1, wherein the word "happy" is embroidered on the left sock and the word "feet" is embroidered on the right sock.

4. The pair of foot alignment socks of claim 1, wherein the toe separators are made from the same material as the sock body.

5. The pair of foot alignment socks of claim 1, wherein the length of the first toe separator is greater than the length of the second and third toe separators and the length of the second and third toe separators is greater than the length of the fourth toe separator.

6. A pair of foot alignment socks comprising:
a left sock and a right sock, each sock comprising:
a sock body having a first open end positionable proximate to the base of the toes of a foot, an upper portion which extends over the top of the foot, an lower portion which extends over the sole of the foot, a heel portion which extends over the heel of the foot and a second open end positionable proximate to the ankle attached to a foot;
a first toe separator positioned to be located between the first toe and the second toe and having a length of 35 mm and a diameter of between 13-17 mm;
a second toe separator positioned to be located between the second toe and the third toe and having a length of 30 mm and a diameter of between 10.5-14.5 mm;
a third toe separator positioned to be located between the third toe and the fourth toe and having a length of 30 mm and a diameter of between 10.5-14.5 mm;
a fourth toe separator positioned to be located between the fourth toe and the fifth toe and having a length of 25 mm and a diameter of between 10.5-14.5 mm;
each toe separator having a generally cylindrical cross-section and being attached at one end to the lower portion of the sock at the first open end and at an opposite end to the upper portion of the sock at the first open end forming a loop; and
wherein the cylindrical cross-section of each toe separator applies pressure to the adjacent toes.

7. The pair of foot alignment socks of claim 6, wherein the sock material is chosen from the group of cotton, acrylic, cashmere, nylon and spandex.

8. The pair of foot alignment socks of claim 6, wherein the word "happy" is embroidered on the left sock and the word "feet" is embroidered on the right sock.

9. The pair of foot alignment socks of claim 6, wherein the toe separators are made from the same material as the sock body.

10. A pair of foot alignment socks comprising:
a left sock and a right sock, each sock comprising:
a sock body having a first open end positionable proximate to the base of the toes of a foot, an upper portion which extends over the top of the foot, a lower portion which extends over the sole of the foot, a heel portion which extends over the heel of the foot and a second open end positionable proximate to the ankle attached to a foot;
a first toe separator positioned to be located between the first toe and the second toe and having a length of 35 mm and a diameter of between 13-17 mm;
a second toe separator positioned to be located between the second toe and the third toe and having a length of 30 mm and a diameter of between 10.5-14.5 mm;
a third toe separator positioned to be located between the third toe and the fourth toe and having a length of 30 mm and a diameter of between 10.5-14.5 mm;
a fourth toe separator positioned to be located between the fourth toe and the fifth toe and having a length of 25 mm and a diameter of between 10.5-14.5 mm;
each toe separator having a generally cylindrical cross-section and being attached at one end to the lower portion of the sock at the first open end and at an opposite end to the upper portion of the sock at the first open end forming a loop,
wherein each sock has a unique identifier designed to aid the user in differentiating between the left and right sock; and
wherein the cylindrical cross-section of each toe separator applies pressure to the adjacent toes.

11. The pair of foot alignment socks of claim 10, wherein the sock material is chosen from the group of cotton, acrylic cashmere, nylon and spandex.

12. The pair of foot alignment socks of claim 10, wherein the word "happy" is embroidered on the left sock and the word "feet" is embroidered on the right sock.

13. The pair of foot alignment socks of claim 10, wherein the toe separators are made from the same material as the sock body.

* * * * *